US011809823B2

(12) United States Patent
Carbonell et al.

(10) Patent No.: US 11,809,823 B2
(45) Date of Patent: Nov. 7, 2023

(54) DYNAMIC OPERATING ROOM SCHEDULER USING MACHINE LEARNING

(71) Applicant: International Business Machines Corporation, Armonk, NY (US)

(72) Inventors: Lee Carbonell, Flower Mound, TX (US); Olivia Loza, Corinth, TX (US); Steven Keller, Euless, TX (US)

(73) Assignee: International Business Machines Corporation, Armonk, NY (US)

( * ) Notice: Subject to any disclaimer, the term of this patent is extended or adjusted under 35 U.S.C. 154(b) by 780 days.

(21) Appl. No.: 15/834,707

(22) Filed: Dec. 7, 2017

(65) Prior Publication Data

US 2019/0180867 A1   Jun. 13, 2019

(51) Int. Cl.
*G16H 40/20* (2018.01)
*G06F 40/237* (2020.01)
(Continued)

(52) U.S. Cl.
CPC ........... *G06F 40/237* (2020.01); *G06N 20/00* (2019.01); *G06V 20/41* (2022.01); *G16H 40/20* (2018.01); *G16H 40/63* (2018.01)

(58) Field of Classification Search
CPC ........ G16H 40/20; G16H 40/63; G16H 20/40; G16H 50/70; G06N 20/00; G06F 40/20; G06F 40/237; G06K 9/00718
See application file for complete search history.

(56) References Cited

U.S. PATENT DOCUMENTS 7,518,502 B2   4/2009  Austin et al.
8,292,184 B2 * 10/2012  Turbovich ............. G06K 7/089
                                                  235/462.45
(Continued)

FOREIGN PATENT DOCUMENTS

EP    1422651 A2 *  5/2004  ......... G06F 19/3418
WO    9725682 A      7/1997
(Continued)

OTHER PUBLICATIONS

Scrupelli, Designing Information Hotspots for the Surgical Suite: How Architecture, Artifacts, and People's Behavior Converge to Support Coordination, Human-Computer Interaction Institute, School of Computer Science, Carnegie Mellon University, May 2009, pp. 1-211.

(Continued)

*Primary Examiner* — Peter H Choi
*Assistant Examiner* — Shyam M Goswami
(74) *Attorney, Agent, or Firm* — Edell, Shapiro & Finnan, LLC

(57) ABSTRACT

A method, system and computer program product are provided. A computing system collects information related to a patient's preparation for a medical procedure and provides information regarding the medical procedure and a medical condition of the patient to at least one member of a medical procedure team. Data pertaining to performance of the medical procedure in an operating room is collected from multiple sensors. Progress of the medical procedure is monitored in real time by analyzing the collected data, a procedure reference library, and a physician history to determine a status of the medical procedure. A schedule of one or more subsequent medical procedures for the operating room is adjusted in real time based on the monitored progress. Notifications of the adjusted schedule may be transmitted to participants of the one or more subsequent medical procedures.

20 Claims, 6 Drawing Sheets

(51) Int. Cl.
*G16H 40/63* (2018.01)
*G06N 20/00* (2019.01)
*G06V 20/40* (2022.01)

(56) References Cited

U.S. PATENT DOCUMENTS

| | | | |
|---|---|---|---|
| 8,799,009 B2 | 8/2014 | Mellin et al. | |
| 9,129,054 B2 | 9/2015 | Nawana et al. | |
| 9,485,475 B2 | 11/2016 | Speier et al. | |
| 2005/0060211 A1* | 3/2005 | Xiao | G16H 40/20 705/6 |
| 2005/0240423 A1* | 10/2005 | Becker | G16H 40/20 705/2 |
| 2006/0282302 A1 | 12/2006 | Hussain | |
| 2008/0046286 A1* | 2/2008 | Halsted | G06Q 50/22 705/2 |
| 2009/0125337 A1* | 5/2009 | Abri | G16H 40/20 705/3 |
| 2009/0132586 A1 | 5/2009 | Napora et al. | |
| 2009/0216558 A1 | 8/2009 | Reisman et al. | |
| 2011/0117878 A1* | 5/2011 | Barash | G08B 21/0211 455/404.2 |
| 2013/0325508 A1* | 12/2013 | Johnson | G06F 19/3418 705/3 |
| 2014/0067413 A1 | 3/2014 | Ghivizzani | |
| 2014/0081659 A1 | 3/2014 | Nawana et al. | |
| 2014/0184772 A1* | 7/2014 | Hanina | H04N 7/18 348/77 |
| 2014/0288941 A1* | 9/2014 | Roady | G16H 40/67 705/2 |
| 2015/0073816 A1 | 3/2015 | Ha et al. | |
| 2015/0081322 A1* | 3/2015 | Woolford | G06Q 50/22 705/2 |
| 2015/0164436 A1 | 6/2015 | Maron et al. | |
| 2015/0294089 A1 | 10/2015 | Nichols | |
| 2015/0356198 A1* | 12/2015 | D'Souza | G16H 40/20 705/2 |
| 2016/0004831 A1* | 1/2016 | Carlson | G16H 10/20 705/2 |
| 2016/0180743 A1* | 6/2016 | Ahmad | G16H 30/40 434/262 |
| 2016/0246929 A1 | 8/2016 | Zenati et al. | |
| 2016/0350499 A1 | 12/2016 | Anjomshoa et al. | |
| 2017/0185930 A1* | 6/2017 | Perry | H04L 67/26 |
| 2018/0150695 A1* | 5/2018 | Guttmann | G06V 20/40 |

FOREIGN PATENT DOCUMENTS

| | | | | |
|---|---|---|---|---|
| WO | 2014159350 A1 | 10/2014 | | |
| WO | WO-2019071185 A1 * | 4/2019 | | G16H 10/20 |
| WO | WO-2019111077 A1 * | 6/2019 | | A61B 34/00 |

OTHER PUBLICATIONS

Park, Advanced Technologies in Safe and Efficient Operating Rooms, University of Maryland Medical Center, Jan. 10, 2009, see p. 11.

* cited by examiner

DYNAMIC OPERATING ROOM SCHEDULER USING MACHINE LEARNING

BACKGROUND

1. Technical Field

Present invention embodiments relate to using natural language processing, video analytics, sensors, IoT devices and machine learning for monitoring progress of a medical procedure in an operating room, updating an operating room schedule, providing notifications to others regarding operating room schedule changes, and updating associated databases.

2. Discussion of the Related Art

According to a recent study, an estimated 250,000 deaths occur in the United States annually due to medical errors. The actual figure may be higher because residential deaths and deaths in nursing home were not included in the study. Deaths due to medical errors may be the third leading cause of death after cancer and heart disease. Every surgeons' goals includes improving care for their patients. When medical errors are reduced, medical costs for patients will decrease in a number of ways positively impacting overall health for all.

SUMMARY

A method, a system, and a computer program product are provided for monitoring and updating information related to a medical procedure. A computing system may collect information from a patient related to preparation for the medical procedure and may provide information regarding the medical procedure and a medical condition of the patient to at least one member of a medical procedure team associated with the medical procedure. Data pertaining to performance of the medical procedure in an operating room may be collected from multiple sensors. Progress of the medical procedure being performed in the operating room may be monitored in real time by analyzing the collected data, a procedure reference library, and a physician history to determine a status of the medical procedure, the computing system having been trained to recognize patterns based on a set of training data including one or more of retrospective and real-time data to analyze the collected data and make a recommendation regarding the status. A schedule of the operating room for one or more subsequent medical procedures may be adjusted based on the monitored progress of the medical procedure in real time. Notification of the adjusted schedule may be generated and transmitted to participants of the one or more subsequent medical procedures.

BRIEF DESCRIPTION OF THE DRAWINGS

Generally, like reference numerals in the various figures are utilized to designate like components.

DETAILED DESCRIPTION

A system, a method and a computer program product are provided for determining whether a patient is properly prepared for a medical procedure, providing a physician with information regarding a medical condition of the patient and the medical procedure to be performed, monitoring a progress of the medical procedure being performed in an operating room, adjusting an operating room schedule as needed and following up with the patient sometime after completion of the medical procedure. Various embodiments may identify physicians associated with the medical procedure and their roles in the medical procedure. Embodiments may further determine whether all required implements are present in the operating room before and after the medical procedure, and may track how the implements are used during the medical procedure.

Figure 1:
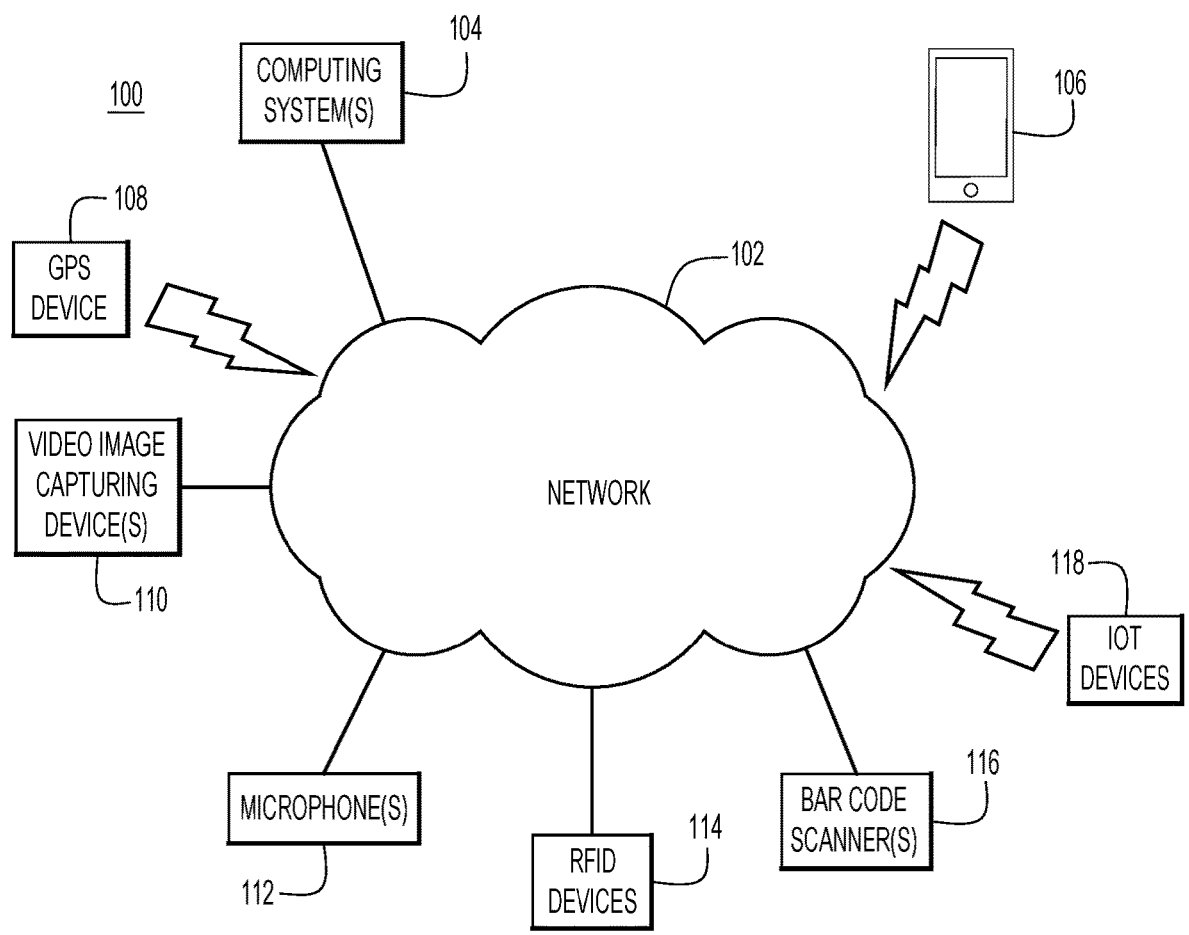
FIG. 1 illustrates an example environment in which embodiments of the invention may operate.

FIG. 1 illustrates an example environment 100 in which present invention embodiments may operate. Example environment 100 may include a network 102, one or more computing systems 104, a handheld or other type of computing device 106, a Global Positioning System (GPS) device 108, one or more video image capturing devices 110, one or more microphones 112, one or more RFID devices 114, one or more barcode scanners 116 and one or more Internet of Things (IoT) devices 118.

Network 102 may include, but not be limited to, a wide area network, a local area network, a packet switching network, the Internet, a cellular telephone data network, or any combination of the above. One or more computing systems 104, handheld or other type of computing device 106, GPS device 108, one or more video image capturing devices 110, one or more microphones 112, one or more RFID devices 114 embedded within, or attached to, medical implements, one or more barcode scanners 116 and one or more Internet of Things (IoT) devices 118 may each be connected to network 102 via a wired or a wireless connection. One or more computing systems 104 may include a server or multiple servers configured as a server farm. Handheld or other type of computing device 106 may include, but not be limited to, a smartphone, a laptop computer, a tablet, a notebook computer, or a desktop computer. GPS device 108 may be a device that obtains location information and reports the location information to one or more computing systems 104 via network 102. One or more video image capturing devices 110 may include a video camera that provides captured video images to one or more computing systems 104 via network 102. One or more microphones 112 may capture speech and other audio information and may provide the captured speech and the other audio information to one or more computing systems 104 via the network 102. RFID devices 114 may provide identifying information regarding respective devices associated therewith. Barcode scanner 116 may scan barcodes and may provide scanned information to computing system 104 via network 102. IoT devices 118 may provide information to one or more computing systems 104 via network 102.

In some embodiments, GPS device 108, handheld or other type of computing device 106 and IoT devices 118 may have wireless connections to network 102. In other embodiments, others of the above-mentioned devices may be connected to network 102 via either a wireless or a wired connection.

Figure 2:
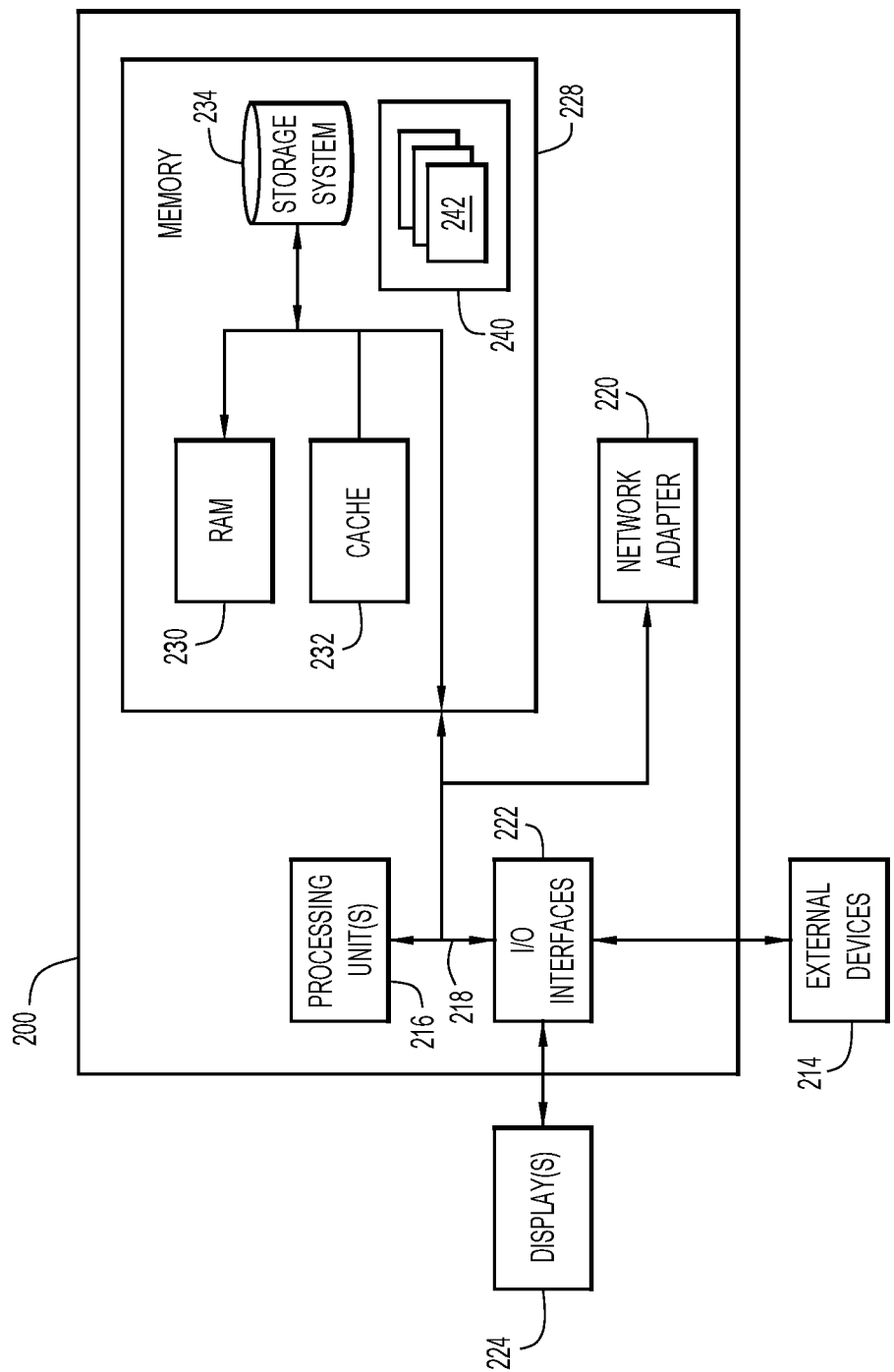
FIG. 2 is a functional block diagram of a computing system that may implement embodiments of the invention.

FIG. 2 is a functional block diagram of a computing system 200 that may implement one or more computing systems 104 in various embodiments of the invention. Computing system 200 is shown in a form of a general-purpose computing device. Components of computing system 200 may include, but are not limited to, one or more processors or processing units 216, a system memory 228, and a bus 218 that couples various system components including system memory 228 to one or more processing units 226.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, one or more displays 224, one or more devices that enable a user to interact with computing system 200, and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

Figure 3:
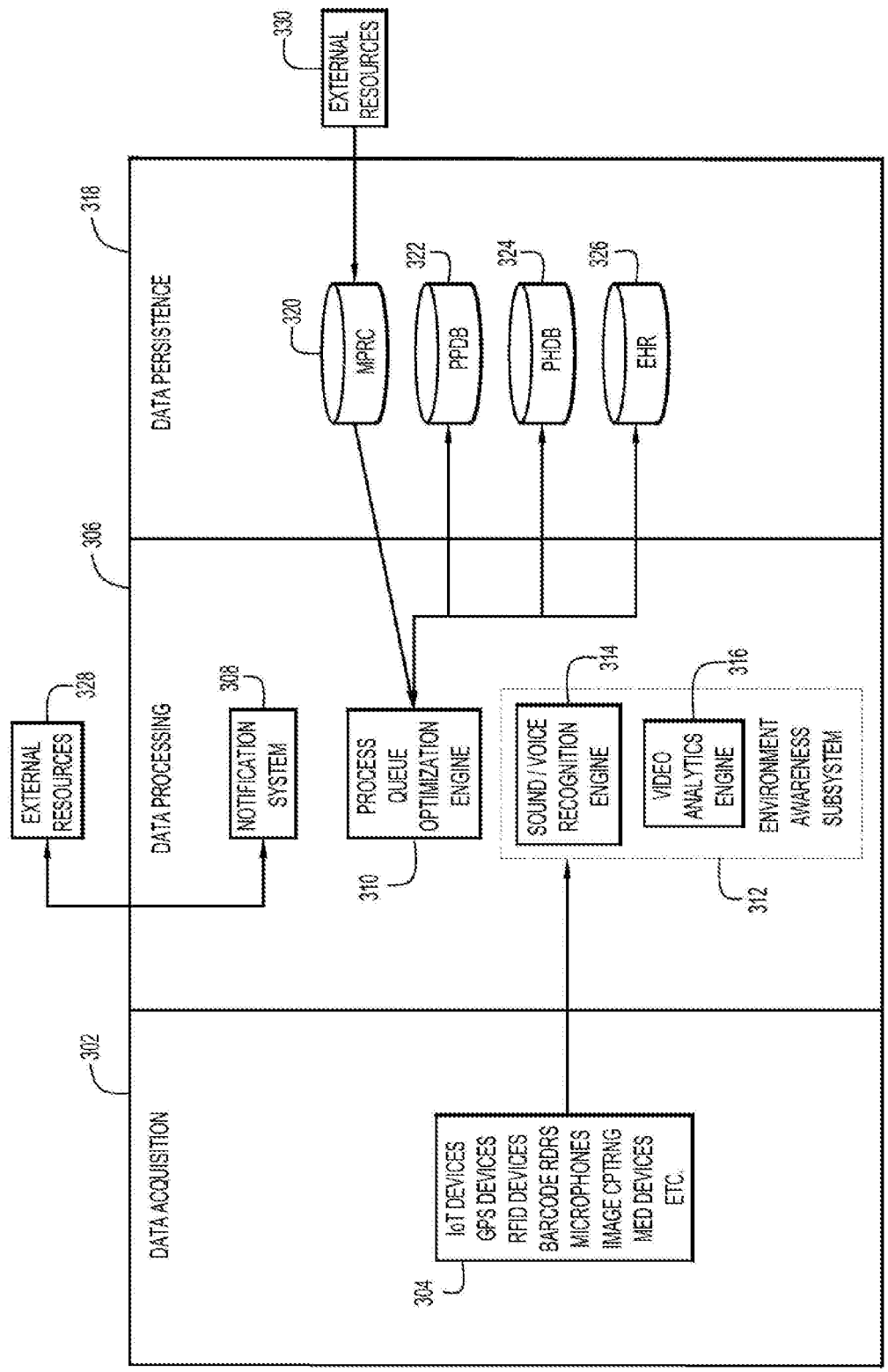
FIG. 3 illustrates multiple layers according to an embodiment of the invention.

Invention embodiments may be segmented into three layers, a data acquisition layer, a processing layer and a data persistence layer. FIG. 3 illustrates the layers of various embodiments.

Data acquisition layer 302 may include various devices 304 that collect information and provide the information to data processing layer 306. Various devices 304 may include, but not be limited to, one or more IoT devices, a GPS device, one or more RFID devices, one or more barcode readers, one or more microphones, one or more video image capturing devices and one or more medical devices or implements.

Data processing layer 306 may include an environment awareness subsystem 312 that receives the collected information provided by data acquisition layer 302. Environment awareness subsystem 312 may include a sound/voice recognition engine 314 and a video analytics engine 316. Sound/voice recognition engine 314 may perform natural language processing and sentiment analysis as it gathers conversations in an operating room to determine a status of a medical procedure. Hearing a surgeon say, "Thank you team, this was excellent work," may be interpreted as indicating that the medical procedure is nearing completion. Similarly, hearing the surgeon say, "Apply stitches to the wound," may also be interpreted as indicating that the medical procedure is nearing completion. Video analytics engine 316 may compare captured video to historical video to determine a status of a medical procedure. Knowing the status of the medical procedure is helpful to environmental awareness subsystem 312 in determining when to prepare and to sanitize the operating room for a next medical procedure. Data processing layer 306 may further include a process queue optimization engine (PQOE) 310 and a notification system 308.

PQOE 310 may include a list of processes to be performed for a given medical procedure. As each medical procedure completes, PQOE 310 may optimize a current schedule for the operating room as well as future schedules for the operating room.

Notification system 308 may communicate with external systems 328 as well as internal systems to ensure that nothing delays the readiness, start and completion of a medical procedure. For example, notification system 308 may notify family members of the patient if a medical procedure is delayed such that the family members are aware of the status of the medical procedure and are aware of when to be present for the patient. The notifications may be provided to external systems 328 via email messages, text messages and phone calls, as well as other means. Some external systems 328 may provide feedback from external systems 328. External systems 328 may include, but not be limited to, a computing system, a handheld computing device, a tablet computing device, a laptop or notebook computing device, a smartphone and a desktop personal computing system. Notification system 308 may further include customized thresholds for determining if, or when, alarms are to be dispatched to various parts of a system.

Data persistence layer 318 may store information related to continuous improvement of care in an operating room. Data persistence layer 318 may include, but not be limited to, a medical procedure reference corpus (MPRC) 320, a physician profile database (PPDB) 322, a procedure history database (PHDB) 324 and an electronic health record (EHR) database 326. Each of PPDB 322, PHDB 324 and EHR 326 may be updated by data processing layer 306.

MPRC 320 may include a list of medical procedures that are performed by a facility. Over time, as new procedures are performed at the facility, the list of medical procedures may be updated. Further, MPRC 320 may ingest external resources 330 such as, for example, medical journals and other external resources, to ensure that medical standards, procedures and best practices are kept up-to-date.

PPDB 322 may include a list of physician profiles that describe each physician's qualifications and specialties. PPDB 322 may also contain a list of procedures in which respective physicians specialize. As a physician acquires new skills and performs or participates in new medical procedures, PPDB 322 may be updated. PPDB 322 further may include information regarding roles that a physician plays in each procedure in which he or she participated. For example, PPDB 322 may include information regarding a medical procedure and whether a physician was a lead, an assistant or an observer. PPDB 322 may further include a list of procedure categories, with physicians assigned to respective procedure categories.

While training, testing and validating processes concerning medical procedures, embodiments of the invention may learn patterns based on historical data and real-time data provided by multiple sensors. Further, patterns may be learned based on feedback provided by medical procedure teams performing the medical procedures.

Figure 4:
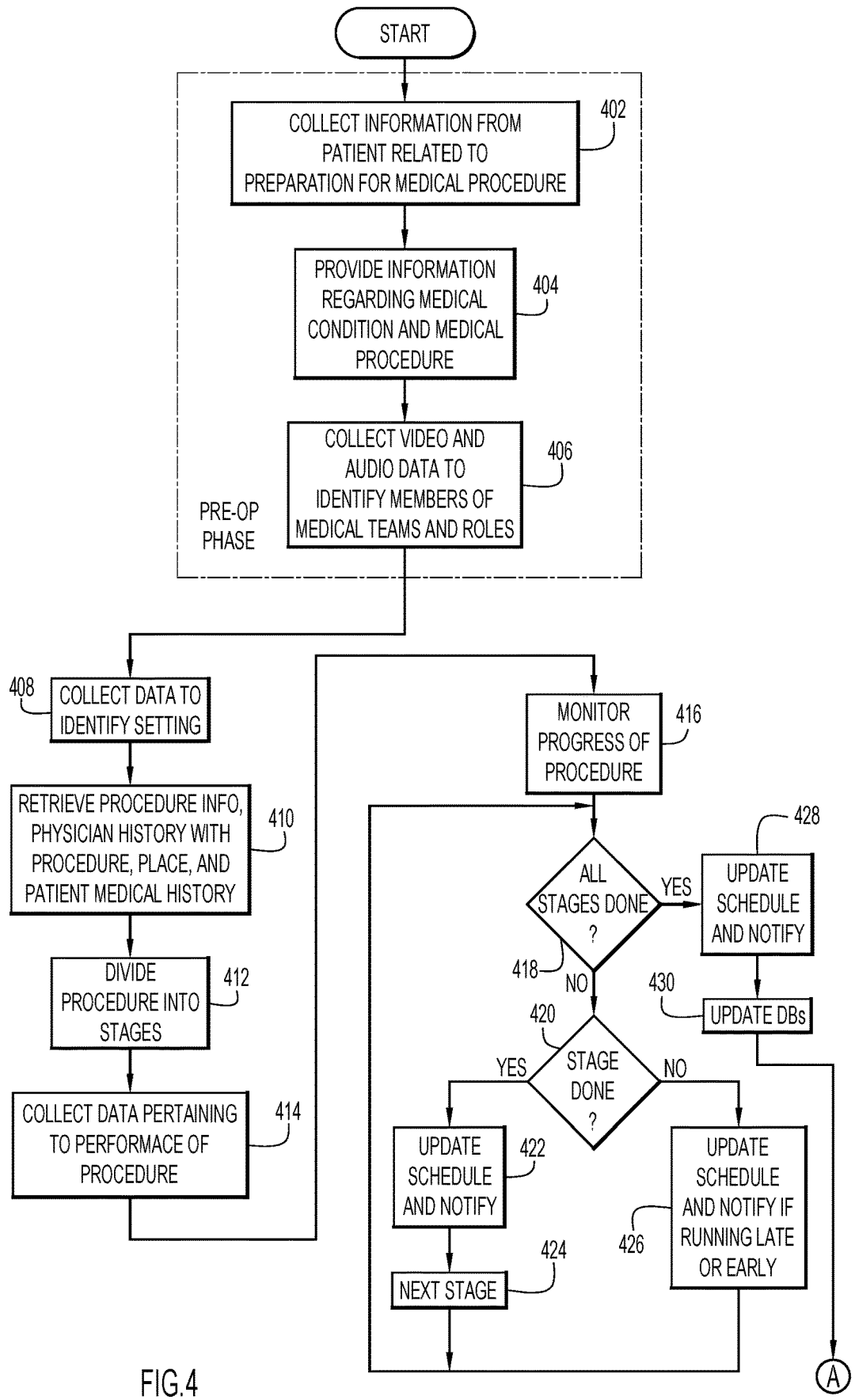
FIGS. 4 and 5 are flowcharts that illustrate an example process that may be performed according to embodiments of the invention.
Figure 5:
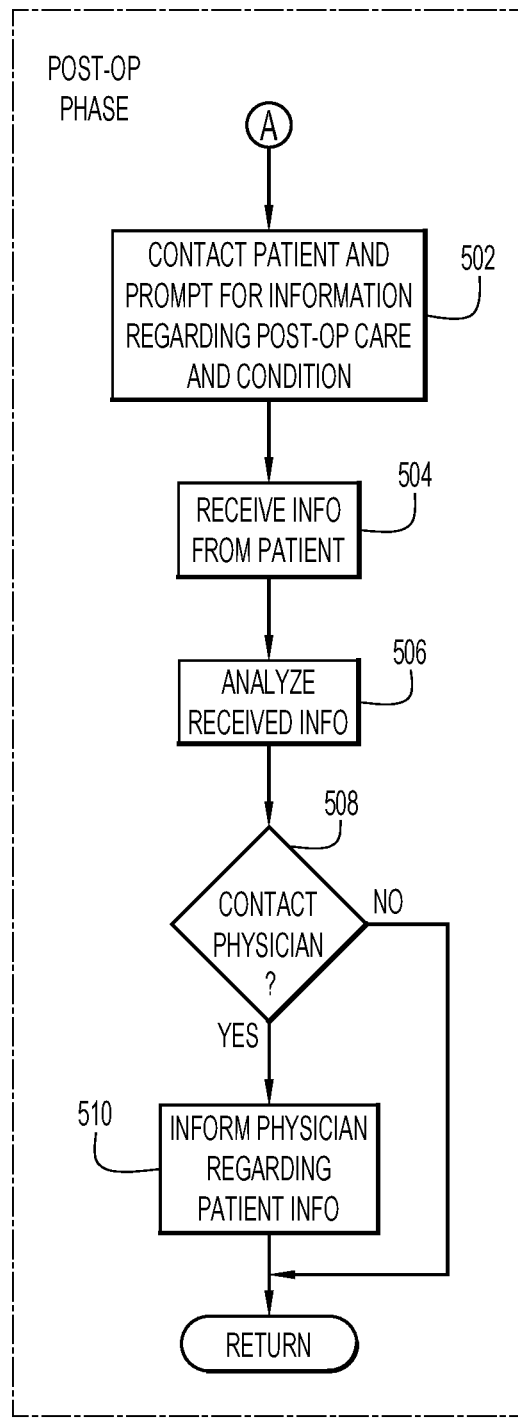

FIGS. 4 and 5 are flowcharts that illustrate an example process that may be performed in embodiments of the invention. The process may begin with information, related to preparation for a medical procedure, being collected from a patient (act 402). The patient may be contacted, via notification system 308, by one or more computing systems 104 and prompted to provide the information via an email, a text message, a phone call or other methods. For example, the patient may receive an email message, text message or phone call asking whether the patient fasted that morning, etc. Responses provided by the patient may be received by notification system 308 and provided to PQOE 310.

Information regarding a medical condition of the patient and a medical procedure to be performed on the patient may be collected by one or more computing systems 104 from EHR 326 and may be provided to one or more members of a medical procedure team such as, for example, a physician of the patient using notification system 308 (act 404).

When members of the medical team meet to discuss their respective roles and the medical procedure to be performed, one or more computing systems 104 may collect video and audio data from corresponding devices and may identify members of the medical team using image analysis and voice signature recognition techniques (act 406). The image analysis may further include facial recognition techniques. Natural language processing and voice signature recognition techniques may also be used to determine respective roles of members of the medical team (act 406).

Next, in an operating room, data may be collected from a number of devices 304 by data acquisition layer and may be provided to one or more computing devices 104 (act 408). Thus, data may be collected from, for example, one or more video image capturing devices, a GPS device, one or more RFID devices attached to, or embedded within, medical implements, one or more barcode readers, one or more microphones, etc. The collected data may be processed by environment awareness subsystem 312 to identify people in the operating room including the patient, a location of the operating room, medical implements available in the operating room, etc.

One or more computing systems 104 may retrieve medical procedure information from PHDB 324 and MPRC 320, a physician's history regarding the medical procedure performed and a place where the procedure was performed from PPDB 322, and a medical history of the patient from EHR 326 (act 410).

Data processing layer 306 executing on one or more computing systems 104 may divide the medical procedure into multiple stages (act 412). Data pertaining to performance of the medical procedure may continue to be collected (act 414) and progress of the medical procedure may be continuously monitored (act 416).

For example, during the medical procedure, text may be extracted from collected audio information and natural language processing may be applied to the extracted text to determine the progress of the medical procedure. In addition, embodiments of the invention may annotate the text with appropriate International Classification of Diseases, Tenth revision, (ICD-10) codes or other codes.

Video analytics engine 316 may use cognitive analytics to determine whether steps included in the medical procedure are effectively executed, and if a determination is made that a stage of the medical procedure is taking longer than expected, embodiments may provide real-time suggestions based on previous successful medical procedures. In addition, video analytics engine 316 may analyze and compare captured video images with previously stored video images from a same type of medical procedure to determine the progress. If the system determines that a wrong patient is to have the medical procedure performed thereon, an unqualified doctor is to lead the medical procedure, or a wrong body part is about to be involved in the medical procedure, an alarm may be generated and a warning distributed via notification system 308. In some embodiments, a speaker in an operating room may receive an audio warning message which may be played through the speaker.

Data processing layer 306 may determine whether all stages of the medical procedure are completed (act 418). If all of the stages are determined not to be completed, then data processing layer 306 may determine whether a current stage is completed (act 420). If the current stage is determined to be completed, then process queue optimization engine (PQOE) 310 may update a current schedule for one or more operating rooms and may notify affected medical teams of the updated schedule via notification system 308 (act 422). A current stage of the medical procedure may be changed to a next stage (act 424) and processing may then continue with act 418. Otherwise, if the current stage is determined to be uncompleted during act 420, then PQOE 310 may update a current schedule regarding any changes and may notify the affected medical teams whether the medical procedure is running early or late (act 426). Processing may then continue with act 418.

If, during act 418, all stages are determined to be completed, then environment awareness subsystem 312 may account for the instruments used during the procedure, PQOE 310 may update the schedule for one or more operating rooms and notification system 308 may send notifications to affected medical teams as well as one or more family members of the patient (act 428). Data processing layer 306 may then update databases in data persistence layer 318 (act 430). For example, PHDB 324, PPDB 322, EHR 326 and MPRC 320 may be updated.

In some embodiments, automatic annotation may be performed based on the monitored progress. For example, a lead physician may comment on a condition of an organ and a record in EHR 326 for the patient may be annotated. Manual annotation of databases also may be enabled. Metadata may be generated and recorded as media files are stored. In some embodiments, the metadata and/or annotations may include diagnostic codes such as, for example, International Classification of Diseases, Tenth Revision (ICD-10) codes.

FIG. 5 illustrates example processing in a postoperative phase with respect to the medical procedure. The process may begin, sometime after the procedure is completed, by having notification system 308 contact the patient via a phone call, an email, a text message, or other means to request information regarding a condition of the patient and a status of postoperative care (act 502). Notification system 308 may receive a response from the patient (act 504) and may analyze the received response using natural language processing (act 506). A determination may be made regarding whether a physician of the patient is to be contacted (act 508). For example, if the patient is not following instructions for the postoperative care or the condition of the patient has deteriorated, then the determination may be that the physician of the patient should be contacted.

If the determination is that the physician of the patient is to be contacted, then notification system 308 may contact the physician and may provide information regarding postoperative care and the condition of the patient (act 510).

Figure 6:
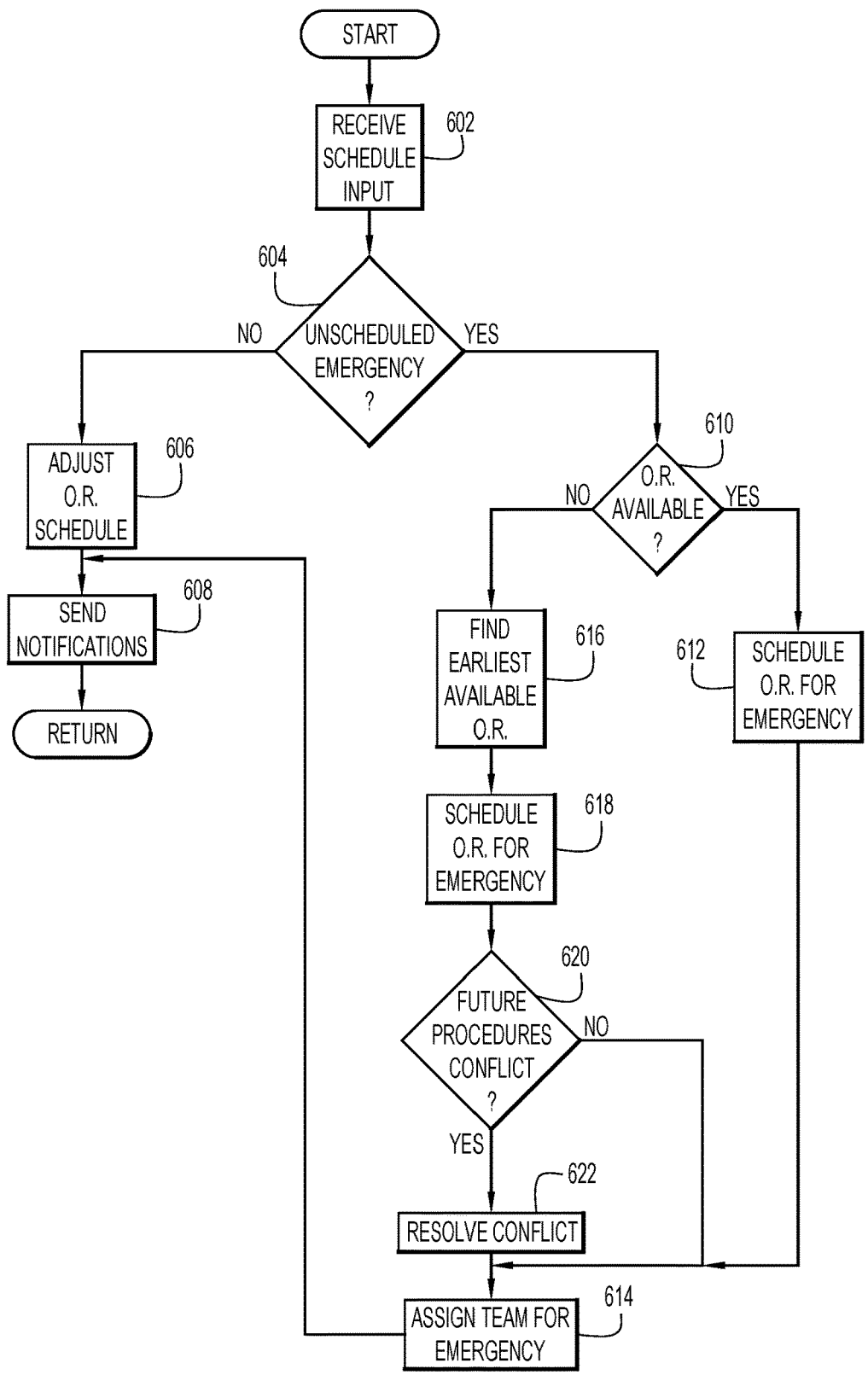
FIG. 6 is a flowchart of an example process for adjusting a schedule for one or more operating rooms based on either a monitored progress of a medical procedure or a request regarding an unscheduled emergency medical procedure according to embodiments of the invention.

In some embodiments, in an unscheduled emergency, an operating room schedule may be adjusted to accommodate the emergency. FIG. 6 is a flowchart of an example process for rescheduling an operating room when an unscheduled emergency occurs. The process may begin with the PQOE 310 receiving input related to scheduling an operating room (act 602). PQOE 310 may then determine whether the received input is a request related to an unscheduled emergency or is a request to adjust an operating room schedule based on progress of a monitored medical procedure in an operating room (act 604).

If the received input is a request to adjust an operating room schedule based on the monitored progress of a medical procedure in the operating room, then a schedule for the operating room may be adjusted (act 606) and notification system 308 may notify affected medical teams and, possibly, one or more family members of a patient (act 608). For example, if the medical procedure took 30 minutes longer than expected to complete and several medical procedures are scheduled for the same operating room, one after another, then the schedule may be adjusted such that each of the several medical procedures may be scheduled to begin 30 minutes later than originally scheduled. Additionally, when a facility has multiple operating rooms, availability of the multiple operating rooms may be taken into consideration when adjusting a schedule for any of the operating rooms. For example, if a medical procedure in one of the operating rooms took 30 minutes longer than expected, one or more subsequent medical procedures may be scheduled for other respective available operating rooms.

If, during act 604, the received input is determined to be related to a request for an operating room due to the unscheduled emergency, then PQOE 310 may make a determination regarding whether an operating room is available (act 610). An operating room may be considered to be available if the operating room is not currently being used for a medical procedure. If PQOE 310 determines that an operating room is available, then PQOE 310 may schedule the operating room for the emergency (act 612). PPDB 322 may be accessed to select an available physician with proper qualifications for performing an emergency medical procedure related to the unscheduled emergency and may assign a remainder of a medical team for the emergency medical procedure (act 614). Various embodiments may select a best qualified available physician to perform the emergency medical procedure. Notification system 308 may then notify medical team regarding the scheduled operating room for the emergency medical procedure and may provide any available medical information about an emergency patient (act 608).

If, during act 610, a determination is made that no operating room is available, then PQOE 310 may determine how soon an earliest available operating room may be available based on monitoring progress of one or more ongoing medical procedures and an urgency regarding any next scheduled medical procedure for that operating (act 616). PQOE 310 may schedule the emergency medical procedure for the earliest available operating room (act 618). If a conflict is determined regarding a scheduled medical procedure for the operating room (act 620), then PQOE 310 may resolve the conflict (act 622). For example, if a medical procedure with a same level of urgency as the emergency medical procedure is scheduled to use the operating room, the conflict may be resolved by finding another available operating room in a same facility, or, if absolutely necessary, the conflict may be resolved by finding an available operating room in a nearby facility. If the medical procedure has a lower level of urgency than the emergency medical procedure, then the emergency medical procedure may continue to be scheduled to use the operating room and the previously scheduled medical procedure may be scheduled to use another available operating room in a same facility, or may be delayed until an operating room becomes available.

As previously discussed, PQOE 310 may assign an available qualified physician for the emergency medical procedure (act 614). Notification system 308 may notify the assigned qualified physician as well as members of an emergency medical team and may further notify other medical teams affected by any change in schedule (act 608).

Historical video data, audio data and annotations pertaining to medical procedures may be used to identify trends and patterns that are used as feedback for machine learning to improve accuracy of progress determinations, validate results and improve future medical procedures. The medical team may be prompted for a checklist and suggestions as a systematic alert and the checklist and suggestions may be adjudicated for relevance to the medical procedure. In addition, an operating room schedule may be personalized based on historical evidence of average medical procedure times and a length of time an attending physician typically takes to perform the medical procedure.

It will be appreciated that the embodiments described above and illustrated in the drawings represent only a few of the many ways of implementing embodiments. The environment of the present invention embodiments may include any number of computer or other processing systems and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database systems may be included within or coupled to the server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of monitoring a medical procedure, the method comprising:
   collecting, by a plurality of sensors, data pertaining to performance of the medical procedure in an operating room of a facility having a plurality of operating rooms, wherein the plurality of sensors includes a video image capture device and an audio capture device and the collected data include video images and audio of the performance of the medical procedure, and wherein the medical procedure is a surgical procedure using a medical instrument;
   determining, by a computing system, members of a medical team performing the medical procedure and roles of the members of the medical team by analyzing the audio and video images via image processing, natural language processing, and voice recognition techniques;
   monitoring, by the computing system, progress of the medical procedure in the operating room in real time by analyzing the collected data, a procedure reference library, and a physician history to determine a status of the medical procedure, wherein analyzing the collected data includes:
      identifying certain phrases indicating the medical procedure is completing and a role of a member of the medical team providing the certain phrases by analyzing the audio and video images via image processing, natural language processing, and voice recognition techniques;

comparing, via image analysis techniques, the video images of the performance of the medical procedure of the collected data with previously stored video images from performance of a same type of medical procedure that was performed prior to the medical procedure to determine whether a stage of the medical procedure using the medical instrument takes longer than an expected amount of time; and determining that the operating room is used longer than a scheduled amount of time for the medical procedure based on the identified phrases and the role of the member providing the identified phrases of the analyzed audio indicating the medical procedure is completing and the comparing of the video images of the collected data with the previously stored video images indicating the stage of the medical procedure using the medical instrument takes longer than the expected amount of time;

adjusting, by the computing system in real time, use of one or more operating rooms in an electronic operating room schedule by dynamically rescheduling performance of one or more subsequent medical procedures in the electronic operating room schedule in real time based on the medical procedure taking longer than the scheduled amount of time; and generating and transmitting notifications of the adjusted use over a network to devices of participants of the one or more subsequent medical procedures.

2. The method of claim 1, wherein:
the analyzing the collected data further comprises applying video analytics to the video images of the collected data to determine the progress of the medical procedure, and the method further comprises:
using, by the video analytics, cognitive analysis to determine whether a plurality of steps included in the medical procedure are executed effectively, and
determining, by the video analytics, whether instruments used in the medical procedure are accounted for before the medical procedure and after the medical procedure.

3. The method of claim 2, further comprising:
annotating text extracted from the audio of the collected data with appropriate international classification of disease codes to facilitate future analysis of medical procedures.

4. The method of claim 1, wherein:
the plurality of sensors includes at least one from a group consisting of an RFID sensor and a bar code reader, and
the collected data pertaining to performance of the medical procedure includes data for tracking use of medical implements during the medical procedure.

5. The method of claim 1, wherein determining members of the medical team is performed via at least one from a group consisting of facial recognition techniques and a verbal signature.

6. The method of claim 1, further comprising:
partitioning the medical procedure into a plurality of stages, wherein:
the monitoring the progress of the medical procedure further comprises monitoring the progress of each of the plurality of stages, the monitoring the progress of each of the plurality of stages further comprising:
determining whether a respective stage is taking longer than the expected amount of time, and
providing real-time suggestions, based on previous successful medical procedures, to improve the medical procedure when the respective stage is determined to be taking longer than the expected amount of time;

the adjusting the use of the one or more operating rooms further comprises adjusting availability of the use of the one or more operating rooms for the one or more subsequent medical procedures based on the monitored progress of the each of the plurality of stages, and when the monitoring of the progress of the medical procedure determines a completion of all of the plurality of stages, providing a notification regarding an end of the medical procedure to at least one individual associated with the patient.

7. The method of claim 1, further comprising:
storing the collected data pertaining to the performance of the medical procedure to provide a history of medical procedures, and wherein:
the adjusting the use of the one or more operating rooms further comprises adjusting availability of the one or more operating rooms for the one or more subsequent medical procedures utilizing machine learning based on the history of medical procedures.

8. The method of claim 1, further comprising:
automatically contacting a patient after the medical procedure regarding post-operative patient care;
receiving feedback from the patient regarding the post-operative patient care;
determining, based on the received feedback, whether to contact a physician regarding the received feedback; and
automatically contacting the physician when the determining determines to contact the physician regarding the received feedback.

9. A system for monitoring a medical procedure, the system comprising:
at least one memory;
a plurality of sensors; and
at least one processor connected to the at least one memory and the plurality of sensors, the at least one processor being configured to perform:
collecting data from the plurality of sensors pertaining to performance of the medical procedure in an operating room of a facility having a plurality of operating rooms, wherein the plurality of sensors includes a video image capture device and an audio capture device and the collected data include video images and audio of the performance of the medical procedure, and wherein the medical procedure is a surgical procedure using a medical instrument;
determining members of a medical team performing the medical procedure and roles of the members of the medical team by analyzing the audio and video images via image processing, natural language processing, and voice recognition techniques;
monitoring progress of the medical procedure in the operating room in real time by analyzing the collected data, a procedure reference library, and a physician history to determine a status of the medical procedure, wherein analyzing the collected data includes:
identifying certain phrases indicating the medical procedure is completing and a role of a member of the medical team providing the certain phrases by analyzing the audio and video images via image processing, natural language processing, and voice recognition techniques;

comparing, via image analysis techniques, the video images of the performance of the medical procedure of the collected data with previously stored video images from performance of a same type of medical procedure that was performed prior to the medical procedure to determine whether a stage of the medical procedure using the medical instrument takes longer than an expected amount of time; and determining that the operating room is used longer than a scheduled amount of time for the medical procedure based on the identified phrases and the role of the member providing the identified phrases of the analyzed audio indicating the medical procedure is completing and the comparing of the video images of the collected data with the previously stored video images indicating the stage of the medical procedure using the medical instrument takes longer than the expected amount of time;

adjusting, in real time, use of one or more operating rooms in an electronic operating room schedule by dynamically rescheduling performance of one or more subsequent medical procedures in the electronic operating room schedule in real time based on the medical procedure taking longer than the scheduled amount of time; and generating and transmitting notifications of the adjusted use over a network to devices of participants of the one or more subsequent medical procedures.

10. The system of claim 9, wherein:
the analyzing the collected data further comprises:
applying video analytics to the video images of the collected data to determine the progress of the medical procedure,
using cognitive analysis to determine whether a plurality of steps included in the medical procedure are executed effectively,
annotating text extracted from the audio of the collected data with appropriate international classification of disease codes to facilitate future analysis of medical procedures, and
determining, by the video analytics, whether instruments used in the medical procedure are accounted for before the medical procedure and after the medical procedure.

11. The system of claim 9, wherein:
the plurality of sensors includes at least one from a group consisting of an RFID sensor and a bar code reader, and
the collected data pertaining to performance of the medical procedure include data for tracking use of medical implements during the medical procedure.

12. The system of claim 9, wherein determining members of the medical team is performed via at least one from a group consisting of: facial recognition techniques and a verbal signature.

13. The system of claim 9, wherein:
the at least one processor is further configured to perform:
partitioning the medical procedure into a plurality of stages, wherein:
the monitoring the progress of the medical procedure further comprises monitoring the progress of each of the plurality of stages, the monitoring the progress of each of the plurality of stages further comprising:
determining whether a respective stage is taking longer than the expected amount of time, and
providing real-time suggestions, based on previous successful medical procedures, to improve the medical procedure when the respective stage is determined to be taking longer than the expected amount of time;
the adjusting the use of the one or more operating rooms further comprises adjusting availability of the use of the one or more operating rooms for the one or more subsequent procedures based on the monitored progress of the each of the plurality of stages, and
when the monitoring of the progress of the medical procedure determines a completion of all of the plurality of stages, providing a notification regarding an end of the medical procedure to at least one individual associated with the patient.

14. The system of claim 9, wherein the at least one processor is further configured to perform:
storing the collected data pertaining to the performance of the medical procedure to provide a history of medical procedures, and wherein:
the adjusting the use of the one or more operating rooms further comprises adjusting availability of the one or more operating rooms for the one or more subsequent medical procedures utilizing machine learning based on the history of medical procedures.

15. The system of claim 9, wherein the at least one processor is further configured to perform:
maintaining a list of procedure categories, each of a plurality of physicians being assigned to a respective given procedure category; and
responsive to an urgent request for a given medical procedure, determining who will lead the given medical procedure and who will be included in a medical procedure team for the given medical procedure based on the maintained list of procedure categories and the each of the plurality of physicians assigned to the respective given procedure category.

16. A computer program product comprising:
at least one computer readable storage medium having computer readable program code embodied therewith for execution on at least one processor of a computing system, the computer readable program code being configured to be executed by the at least one processor to perform:
collecting data from a plurality of sensors pertaining to performance of a medical procedure in an operating room of a facility having a plurality of operating rooms, wherein the plurality of sensors includes a video image capture device and an audio capture device and the collected data include video images and audio of the performance of the medical procedure, and wherein the medical procedure is a surgical procedure using a medical instrument;
determining members of a medical team performing the medical procedure and roles of the members of the medical team by analyzing the audio and video images via image processing, natural language processing, and voice recognition techniques;
monitoring progress of the medical procedure in the operating room in real time by analyzing the collected data, a procedure reference library, and a physician history to determine a status of the medical procedure, wherein analyzing the collected data includes:

identifying certain phrases indicating the medical procedure is completing and a role of a member of the medical team providing the certain phrases by analyzing the audio and video images via image processing, natural language processing, and voice recognition techniques;

comparing, via image analysis techniques, the video images of the performance of the medical procedure of the collected data with previously stored video images from performance of a same type of medical procedure that was performed prior to the medical procedure to determine whether a stage of the medical procedure using the medical instrument takes longer than an expected amount of time; and determining that the operating room is used longer than a scheduled amount of time for the medical procedure based on the identified phrases and the role of the member providing the identified phrases of the analyzed audio indicating the medical procedure is completing and the comparing of the video images of the collected data with the previously stored video images indicating the stage of the medical procedure using the medical instrument takes longer than the expected amount of time;

adjusting, in real time, use of one or more operating rooms in an electronic operating room schedule by dynamically rescheduling performance of one or more subsequent medical procedures in the electronic operating room schedule in real time based on the medical procedure taking longer than the scheduled amount of time; and generating and transmitting notifications of the adjusted use over a network to devices of participants of the one or more subsequent medical procedures.

17. The computer program product of claim 16, wherein: the analyzing the collected data further comprises:

applying video analytics to the video images of the collected data to determine the progress of the medical procedure, using cognitive analysis to determine whether a plurality of steps included in the medical procedure are executed effectively, and annotating text extracted from the audio of the collected data with appropriate international classification of disease codes to facilitate future analysis of medical procedures.

18. The computer program product of claim 17, wherein the applying the video analytics to the video images of the collected data to determine the progress of the medical procedure further comprises:

reviewing a tray to ensure that a plurality of implements are available, and determining how the medical procedure is progressing based on use of ones of the plurality of instruments.

19. The computer program product of claim 16, wherein:

the plurality of sensors includes at least one from a group consisting of an RFID sensor and a bar code reader, and the collected data pertaining to performance of the medical procedure include data for tracking use of medical implements during the medical procedure.

20. The computer program product of claim 16, wherein the computer readable program code is configured to be executed by the at least one processor to perform:

partitioning the medical procedure into a plurality of stages, wherein:

the monitoring the progress of the medical procedure further comprises monitoring the progress of each of the plurality of stages, the adjusting the use of the one or more operating rooms further comprises adjusting availability of the use of the one or more operating rooms for the one or more subsequent procedures based on the monitored progress of the each of the plurality of stages, and when the monitoring of the progress of the medical procedure determines a completion of all of the plurality of stages, providing a notification regarding an end of the medical procedure to at least one individual associated with the patient.

* * * * *